(12) United States Patent
Kaluzna

(10) Patent No.: US 8,388,608 B1
(45) Date of Patent: Mar. 5, 2013

(54) METHOD AND IMPLANT FOR ATTACHMENT OF THE TRANSPLANTED CORNEA

(75) Inventor: Agnieszka Kaluzna, Bydgoszcz (PL)

(73) Assignee: Indywidualna Specjalistyczna Praktyka Lekarska Dr Med. Bartlomiej Kaluzny, Bydgoszcz (PL)

( * ) Notice: Subject to any disclaimer, the term of this patent is extended or adjusted under 35 U.S.C. 154(b) by 0 days.

(21) Appl. No.: 13/279,811

(22) Filed: Oct. 24, 2011

(51) Int. Cl.
*A61B 18/18* (2006.01)
(52) U.S. Cl. ............................................. 606/4; 606/5
(58) Field of Classification Search .................. 606/4, 5; 128/898
See application file for complete search history.

(56) References Cited

U.S. PATENT DOCUMENTS

| 8,142,423 | B2 * | 3/2012 | Raksi et al. ........................ 606/4 |
| 2002/0072796 | A1 * | 6/2002 | Hoffmann et al. ............ 623/6.43 |
| 2006/0100612 | A1 * | 5/2006 | van der Heyd et al. ........... 606/4 |
| 2007/0239274 | A1 * | 10/2007 | Kellan .......................... 623/6.44 |
| 2007/0244472 | A1 * | 10/2007 | Kuhn et al. ....................... 606/4 |

* cited by examiner

*Primary Examiner* — Bill Thomson
*Assistant Examiner* — Jeffrey Lipitz
(74) *Attorney, Agent, or Firm* — Katten Muchin Rosenman LLP

(57) ABSTRACT

The transplanted cornea attachment method in eye microsurgery and the implant for attaching transplanted corneas, both donor and artificial, without the use of sutures consisting in the cutting of a fragment of the donor tissue (2) and, subsequently, the incision of the corresponding fragment (1) in the recipient tissue (3) so that the donated fragment (2) and the recipient incision (1) have teeth that interlock with each other, and the circular incision (5) in the stroma of the donor and recipient corneal stroma which is less in diameter in the donor tissue and more in diameter in the recipient tissue wherein the fastening implant (4) is subsequently inserted.

5 Claims, 1 Drawing Sheet

METHOD AND IMPLANT FOR ATTACHMENT OF THE TRANSPLANTED CORNEA

BACKGROUND OF THE INVENTION

The patentable subject matter is eye microsurgery method of the transplanted cornea attachment and the implant used for attaching transplanted corneas, both donor corneas and artificial corneas, without using sutures used.

The cornea is the front transparent part of the eyeball characterised by a larger curvature. The thinnest part of the cornea is in its centre, where its average thickness ranges from 500-600 µm. Various pathologies may lead to corneal dysfunction necessitating corneal transplantation-replacement of the old damaged tissue with new donor or artificial tissue.

There are three basic types of corneal transplantations. Full thickness transplants (penetrating), front layers transplants (anterior lamellar keratoplasty) and posterior layers transplants (posterior lamellar keratoplasty). Only the last type of the transplants allows donor tissue to be attached without using sutures.

Both anterior lamellar and penetrating keratoplasty require tight suturing of the transplant cornea to the recipient's tissue. Such methods involve manual suturing making them time-consuming and less precise. The post-procedural corneal shape is irregular with high postoperative astigmatism. Sutures that are too loose may result in insufficient wound tightness, risk of infection-related complications and inflammation and, in effect, transplant rejection. On the other hand, too tight stitching results in postoperative disturbances of the corneal shape.

During corneal transplantation (keratoplasty) the donor and recipient tissues are cut in such a way so that they fit with each other. This is done by means of various types of trephines-circular cutting devices having various diameters which are usually disposable. The cutting of the tissue is accomplished by a circular motion. Therefore, trephines can only be used for round transplants. The technical complexity of this procedure results in the donor and recipient tissues not being ideally matched, which has a negative influence on the final result of keratoplasty.

In the recent years, development of laser technology, in particular development of femtosecond laser for corneal surgery, has created new possibilities, also in the field of corneal transplantation. The femtosecond laser is capable of making incisions in any given plane of the cornea with precision of several micrometers. This allows the donor and recipient tissues to be fitted much more precisely. Different modifications of the transplant shape were also proposed to obtain the lowest possible postoperative astigmatism.

Unfortunately, the advantages of using femtosecond lasers in keratoplasty are so far limited by the necessity to put in sutures causing substantial astigmatism which is hard to predict as well as leading to the complications as mentioned above.

SUMMARY OF THE INVENTION

The invention-based solution consists in developing a new method for attaching the donor transplant cornea or artificial cornea without the use of sutures by means of a special implant.

BRIEF DESCRIPTION OF THE DRAWINGS

The invented method and the implant are presented in more detail in the appended illustrative material in the implementation example with FIG. 1 showing the incision in the recipient cornea, FIG. 2 the incision in the donor cornea and FIG. 3 recipient and donor tissue connected using the fastening implant in front view.

DESCRIPTION OF THE PREFERRED EMBODIMENT

Figure 1:
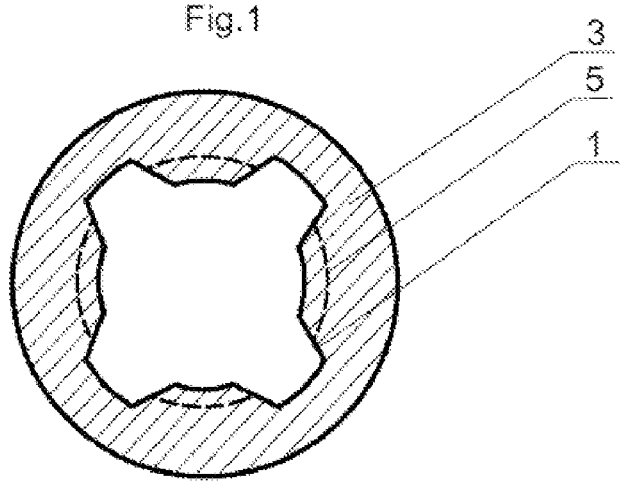
Figure 2:
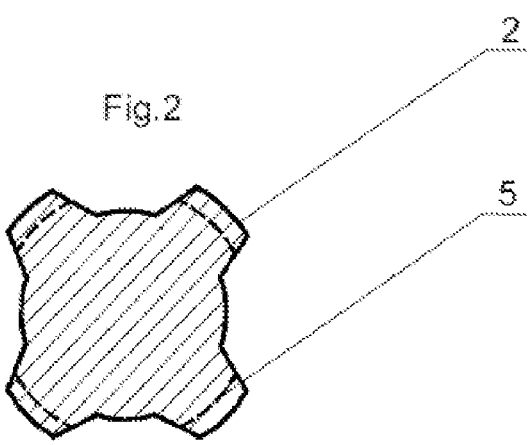
Figure 3:
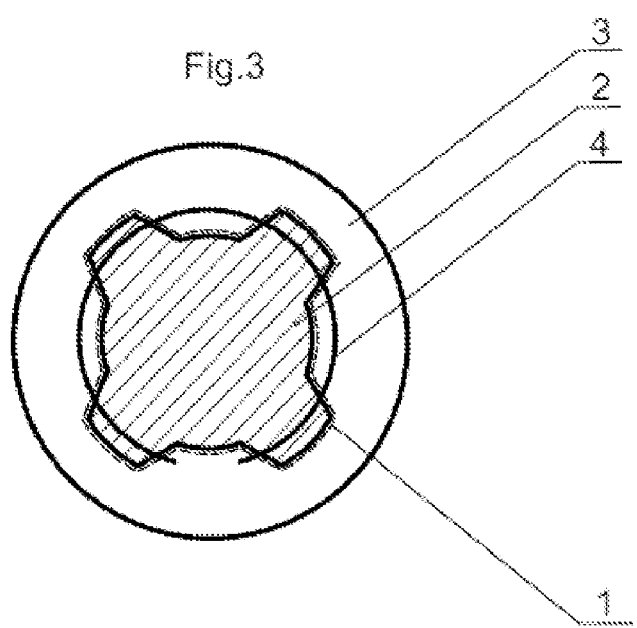

The invention-based transplant cornea attachment method consists in the cutting of a fragment of the donor (2) and recipient tissue (1) using femtosecond laser or other laser with similar properties so that the donor tissue (2) has kind of teeth that mesh with teeth of recipient (1) tissue. A circular incision (5) is made in the donor and recipient corneal stroma creating a type of an intrastromal tunnel where a fastening implant (4) is then inserted allowing the interlocking parts of the tissue to remain connected with each other; the ring-shaped tunnel must be less in diameter in the donor tissue and more in diameter in the recipient tissue so as to ensure tight attachment of the tissues.

The invented implant is made of biocompatible elastic material (e.g. polymethylmetacrylate) and has shape resembling an open ring or its part thus ensuring firm fastening between the meshing corneal tissues of the donor and recipient.

The advantage of the invention-based solution is the possibility of the sutureless transplantation of the donor or artificial cornea. This method eliminates the above mentioned suture-related complications and inconveniences, in particular postoperative astigmatism. Owing to the use of the femtosecond laser, the procedure is very precise and repeatable. The ring-shaped implant stabilises and provides symmetry to the connected tissues thus reducing postoperative refractive errors. The implant can be made of deformable material allowing changes in the corneal curvature even many months after the procedure. The implant may optionally contain an active substance, e.g. anti-infective or immunosuppressive agents.

The invention claimed is:

1. A transplanted cornea attachment method comprising the steps of:
   (a) cutting a corneal fragment having a first diameter from donor tissue using a laser,
      wherein the corneal fragment has a plurality of first teeth extending therefrom
   (b) cutting a tunnel through each of the teach of the corneal fragment;
   (c) cutting an incision in a stroma of a recipient cornea having a second diameter,
      wherein the first diameter is greater than the second diameter, and
      wherein the incision comprises a plurality of teeth;

(d) cutting a tunnel through each of the teeth on the stroma of the recipient cornea;
(e) placing the corneal fragment on the incision so that the teeth on the corneal fragment interlock with the teeth cut in the stroma of the recipient cornea, and
(f) threading an implant through the tunnels formed in the teeth of the corneal fragment and the teeth cut in the stroma of the recipient cornea such that the implant forms a ring and attaches the conical fragment to the stroma of the recipient cornea.

2. The method of claim 1, wherein the implant comprise an anti-infective or immunosuppressive agent.

3. The method of claim 1, wherein the implant is made of a deformable material.

4. The method of claim 1, wherein the implant is formed from a biocompatible elastic material.

5. The method of claim 4, wherein the implant is formed from polymethylmetacrylate.

\* \* \* \* \*